United States Patent
Nie et al.

(10) Patent No.: US 9,526,771 B2
(45) Date of Patent: Dec. 27, 2016

(54) ANTIGEN COMPOSITION, PREPARATION METHOD AND USE THEREOF, AND TUMOR VACCINE

(71) Applicant: National Center for Nanoscience and Technology, Beijing (CN)

(72) Inventors: Guangjun Nie, Beijing (CN); Xin Tian, Beijing (CN); Motao Zhu, Beijing (CN)

(73) Assignee: NATIONAL CENTER FOR NANOSCIENCE AND TECHNOLOGY (CN)

( * ) Notice: Subject to any disclaimer, the term of this patent is extended or adjusted under 35 U.S.C. 154(b) by 70 days.

(21) Appl. No.: 14/394,986

(22) PCT Filed: Feb. 4, 2013

(86) PCT No.: PCT/CN2013/071329
§ 371 (c)(1),
(2) Date: Oct. 16, 2014

(87) PCT Pub. No.: WO2013/155890
PCT Pub. Date: Oct. 24, 2013

(65) Prior Publication Data
US 2015/0093415 A1    Apr. 2, 2015

(30) Foreign Application Priority Data

Apr. 17, 2012 (CN) .......................... 2012 1 0113199

(51) Int. Cl.
*A61K 39/00* (2006.01)
*C12N 5/0784* (2010.01)

(52) U.S. Cl.
CPC ......... *A61K 39/0011* (2013.01); *C12N 5/0639* (2013.01); *A61K 2039/5154* (2013.01); *A61K 2039/5158* (2013.01); *C12N 2501/052* (2013.01); *C12N 2501/22* (2013.01); *C12N 2501/2304* (2013.01)

(58) Field of Classification Search
CPC .............................. A61K 39/00; C12N 5/0639
USPC ....................................... 424/277.1; 435/69.3
See application file for complete search history.

(56) References Cited

FOREIGN PATENT DOCUMENTS

EP    1806395 A1    7/2007
WO   02053176 A2    7/2002

OTHER PUBLICATIONS

Langenkamp, Anja et al. "Kinetics of dendritic cell activation: impact on priming of TH1, TH2 and nonpolarized T cells", Nat Immunol. Oct. 2000;1(4):311-6.
Trajkovic, Katarina et al. "Ceramide Triggers Budding of Exosome Vesicles into Multivesicular Endosomes", Science. Feb. 29, 2008;319(5867):1244-7. doi: 10.1126/science.1153124.
Kovar, Marek et al. "Direct stimulation of T cells by membrane vesicles from antigen-presenting cells", Proc Natl Acad Sci U S A. Aug. 1, 2006;103(31):11671-6. Epub Jul. 19, 2006.
Ahmed, Fariyal et al. "Shrinkage of a Rapidly Growing Tumor by Drug-Loaded Polymersomes: pH-Triggered Release through Copolymer Degradation", Mol Pharm. May-Jun. 2006;3(3):340-50.
Datta, Sandip K. et al. "A Subset of Toll-Like Receptor Ligands Induces Cross-presentation by Bone Marrow-Derived Dendritic Cells", J Immunol. Apr. 15, 2003;170(8):4102-10.
Cornet, Sebastien et al. "CpG oligodeoxynucleotides activate dendritic cells in vivo and induce a functional and protective vaccine immunity against a TERT derived modified cryptic MHC class I-restricted epitope", Vaccine. Mar. 10, 2006;24(11):1880-8. Epub Oct. 28, 2005.
International Search Report mailed in corresponding International Patent Application No. PCT/CN2013/071329 on May 9, 2013, consisting of 11 pp. (English Translation Provided).

*Primary Examiner* — Yan Xiao
(74) *Attorney, Agent, or Firm* — Volpe & Koenig, P.C.

(57) ABSTRACT

The present invention provides a preparation method of an antigen composition. The preparation method comprises the following steps: (1) obtaining a tumor antigen protein; (2) making the tumor antigen protein into contact with an immature dendritic cell; (3) inducing the immature dendritic cell in contact with the tumor antigen into a mature dendritic cell; and (4) separating a cell vesicle of the mature dendritic cell. The present invention further provides an antigen composition obtained through the preparation method and the application thereof in preparing a tumor vaccine.

11 Claims, 1 Drawing Sheet

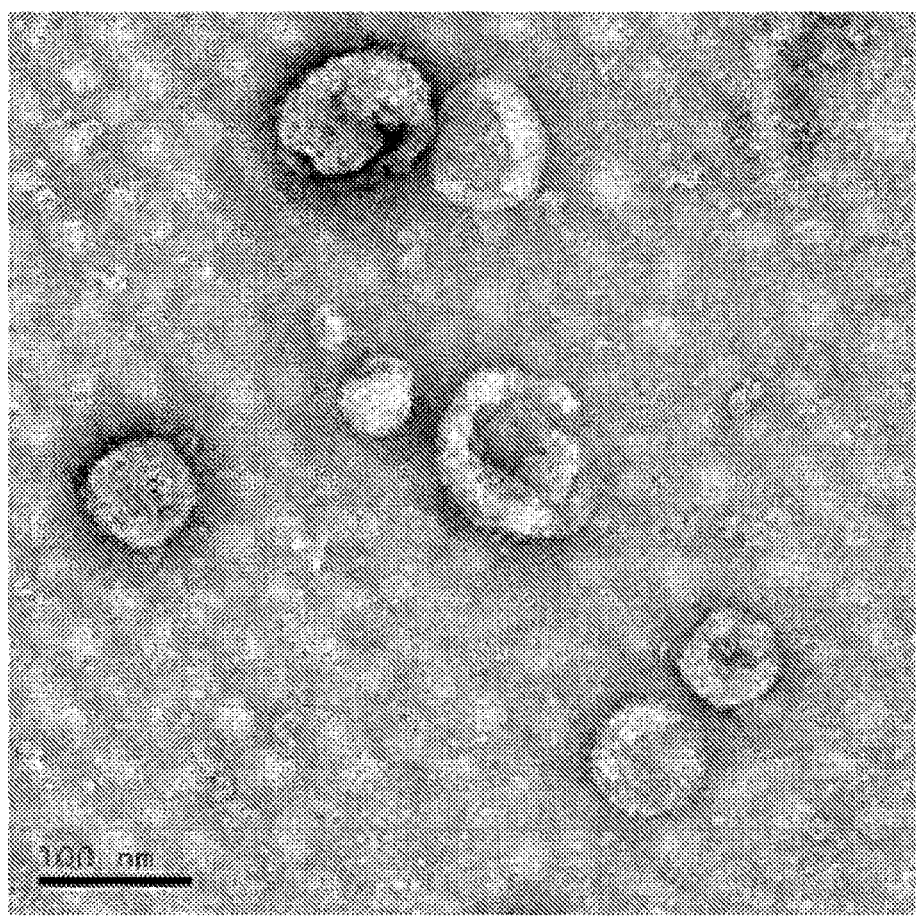

ANTIGEN COMPOSITION, PREPARATION METHOD AND USE THEREOF, AND TUMOR VACCINE

TECHNICAL FIELD

The present invention relates to the field of biomedicine, in particular, relates to an antigen composition, methods for preparing this antigen composition, use of the antigen composition, and a tumor vaccine comprising the antigen composition.

BACKGROUND ART

Current conventional cancer treatments, i.e. surgery, radiotherapy and chemotherapy, are expensive, requires prolonged treatment period, and caused serious damage among cancer patients physically and psychologically. Compared to traditional treatment strategies, immunotherapy is characterized with autologous therapy, causing no damage to the body and a broad antitumor spectrum, particularly suitable for removing small amounts of residual tumor cells, especially dormant tumor cells which are difficult to eradicate by radiotherapy or chemotherapy.

Membrane vesicle is a vesicular structure generated by cells, in a diameter between 30-100 nm, with characteristics such as good stability, long-term storage, etc. It has been found in recent years that membrane vesicle deriving from dendritic cell is a biofilm structure which is suitable for immunotherapy. Many fundamental studies have shown that membrane vesicle produced by dendritic cells loaded with tumor antigens has good immunogenicity, and can effectively activate T lymphocyte cytotoxic response in vivo, kill the tumor cells and have long-term immunological memory. Clinical Phase I studies have shown that such membrane vesicles can effectively prolong survival time of cancer patients, and improve the survival rate of cancer patients, indicating that membrane vesicle can be applied to cancer immunotherapy.

However, there are certain concerns with respect to clinical applications of tumor immunotherapy, for example, firstly, the treatment course is complicated; secondly, the cost of treatment is high; thirdly, it is difficult to completely remove body tumor. To overcome these obstacles, a series of prophylactic tumor vaccines have been developed, such as the human papillomavirus (HPV) vaccine for preventing uterine cervix cancer and hepatitis B virus (HBV) vaccine for preventing liver cancer. However, targets of these prophylactic vaccines are relevant viruses causing tumor rather than the tumor itself, and they can only prevent occurrence of a single type of cancer, therefore there is a limited range of applications. Up to now no one has reported any clinical trials on non-viral prophylactic vaccine based on the tumor itself, or study on vaccine preventing the occurrence of multiple tumors simultaneously. As such, it is necessary to develop a new vaccine which targets tumor itself, and is capable of preventing the occurrence of a variety of tumors.

SUMMARY OF THE INVENTION

In order to overcome the drawback that the existing tumor vaccines can't prevent the occurrence of a variety of tumors, the present invention provides a membrane vesicle vaccine which can prevent occurrence of multiple tumors and its preparation method.

The present inventors have found, when membrane vesicle loaded with a variety of tumor antigen proteins is prepared using tumor-derived tumor antigen protein and membrane vesicle from dendritic cells, mutually promoting effect is produced, so as to stimulate antigen-specific immune responses in vivo more efficiently and with a broader spectrum. Therefore, it could achieve prophylactic effect against a variety of tumors, and better cancer prevention outcome. The present invention is thus developed.

To achieve above object, on one hand, the present invention provides a preparation method of an antigen composition. The preparation method comprises the following steps: (a) mixing soluble protein from melanoma cells with soluble protein from lung adenocarcinoma cells, to obtain tumor antigen protein; or mixing melanoma cells with lung adenocarcinoma cells and extracting soluble protein from the mixed cells, to obtain tumor antigen protein; (2) allowing said tumor antigen protein to get into contact with immature dendritic cells; said immature dendritic cells not only have surface marker phenotype characterized by CD11c negative, CD80 negative, CD86 negative, MHC class I H-2K$^d$ negative and MHC class II I-A$^d$ negative, but also have antigen-presenting activity; (3) after contacting with tumor antigen, inducing the immature dendritic cells into mature dendritic cells; said mature dendritic cells have surface marker phenotype characterized by CD11c positive, CD80 positive, CD86 positive, MHC class I H-2K$^d$ positive and MHC class II I-A$^d$ positive; (4) separating the membrane vesicle of said mature dendritic cells.

On the other hand, the present invention also provides an antigen composition obtained by preparation method described above.

On the other hand, the present invention also provides use of above antigen composition in preparation of tumor vaccine.

On the other hand, the present invention also provides a tumor vaccine comprising above antigen composition and immunoadjuvant.

The above regimen of the present invention can help preventing the occurrence of a variety of tumors.

Other features and advantages of the present invention will be detailed in subsequent embodiment section.

BRIEF DESCRIPTION OF THE DRAWINGS

FIGURES are used to help further understanding of the invention and constitute a part of this specification. Together with the following embodiments, they serve to explain the invention, but do not limit the present invention. Among FIGURES:

FIG. 1 is a transmission electron microscopic (TEM) photo of membrane vesicle obtained from mature dendritic cells in Example 1.

DETAILED DESCRIPTION OF THE EMBODIMENTS

The following will specify embodiments of the present invention in detail. It should be understood that the specific embodiments described herein are only intended to illustrate and explain the present invention, but not to limit the invention.

The present invention provides an preparation method of an antigen composition, which comprises the following steps: (1) mixing soluble protein from melanoma cells with soluble protein from lung adenocarcinoma cells, to obtain tumor antigen protein; or mixing melanoma cells with lung adenocarcinoma cells and extracting soluble protein from the mixed cells, to obtain tumor antigen protein; (2) allowing said tumor antigen protein to get into contact with immature dendritic cells; said immature dendritic cells not only have surface marker phenotype characterized by CD11c negative, CD80 negative, CD86 negative, MHC class I H-2K$^d$ negative and MHC class II I-A$^d$ negative, but also have antigen-presenting activity; (3) after contacting with tumor antigen, inducing the immature dendritic cells into mature dendritic cells; said mature dendritic cells have surface marker phenotype characterized by CD11c positive, CD80 positive, CD86 positive, MHC class I H-2K$^d$ positive and MHC class II I-A$^d$ positive; (4) separating the membrane vesicle of said mature dendritic cells.

Wherein, said melanoma cell is tumor cell from melanoma. It may be obtained by primary dissociation, or purchased commercially. It may also be incubated for amplification with conventional cell culture method. Similarly, said lung adenocarcinoma cell is tumor cell from lung adenocarcinoma. It may be obtained by primary dissociation, or purchased commercially. It may also be incubated for amplification with conventional cell culture method. Typically, said melanoma cell can be the cell purchased from ATCC and with product No. CRL-6475; said lung adenocarcinoma cell can be the cell purchased from ATCC and with product No. CRL-1642.

Wherein, said soluble protein is a protein soluble in water under physiological condition; typically, cell may be broken in phosphate buffer and the insoluble is removed, to yield a solution of the soluble protein. Said phosphate buffer may be various phosphate buffer routinely used for cell engineering, and the present invention has no particular requirement. Wherein, said immature dendritic cell refers dendritic cell which has not conducted antigen-presenting activity yet. Its preparation and identification methods are well known to personnel in this field, e.g., as described in Langenkamp A, et al., *Nature* 2000, 1, 311-316. When a dendritic cell has the surface marker phenotype characterized by CD11c negative, CD80 negative, CD86 negative, MHC class I H-2K$^d$ negative, and MHC class II I-A$^d$ negative, it may be considered as an immature dendritic cell. When a dendritic cell with the surface marker phenotype as described above is alive, it always has antigen-presenting activity.

Wherein, the mature dendritic cell refers to a dendritic cell which has already completed antigen-presenting. A dendritic cell with surface marker phenotype characterized by CD11c positive, CD80 positive, CD86 positive, MHC class I H-2K$^d$ positive and MHC class II I-A$^d$ positive can be considered as mature dendritic cell.

In the present invention, unless otherwise specified, the cell surface marker phenotype are all determined by flow cytometry.

The preparation method based on the present invention, wherein, typically, said immature dendritic cell may be derived from dendritic cell line DC2.4 and/or primary bone marrow mononuclear cell. Wherein, the dendritic cell line DC2.4 is the cell purchased from Southern Cell Technology Limited Company and with product No. CCL-01; said primary bone marrow mononuclear cell may be obtained by isolating it from bone marrow in vitro and culture it; primary bone marrow mononuclear cells may produce immature dendritic cells through conventional induced culture method, e.g., the method recorded in Langenkamp A, et al., *Nature* 2000, 1, 311-316.

The preparation method based on the present invention, wherein, preferably, in step (1), when mixing soluble protein from melanoma cells with soluble protein from lung adenocarcinoma cells, weight ratio of said soluble protein from melanoma cells to said soluble protein from lung adenocarcinoma cells may be 1:0.1-10, more preferably 1:0.5-2; or when mixing melanoma cells with lung adenocarcinoma cells to extract soluble protein, ratio of the number of said melanoma cells to the number of said lung adenocarcinoma cells is 1:0.1-10, more preferably 1:0.2-2.

The preparation method based on the present invention, wherein, preferably, in step (2), with respect to $10^6$ of said immature dendritic cells, the dosage of tumor antigen protein is 1-100 μg, more preferably 10-20 μg. The dosage of the tumor antigen protein may be determined according to conventional protein quantification method, e.g., the Bradford method.

Wherein, the condition allowing said tumor antigen protein to get into contact with immature dendritic cells may be routine cell culture condition, and the present invention has no particular requirement. Preferably, the contact temperature may be 4-42° C., whereas the time may be 1-96 h.

The preparation method based on the present invention, wherein, in step (3), the condition under which the immature dendritic cells are induced into mature dendritic cells after contacting with tumor antigen may be conventional condition under which development of dendritic cell may be induced, such as, condition recorded in Langenkamp A, et al., *Nature* 2000, 1, 311-316, preferably, this condition includes: the immature dendritic cells after in contact with tumor antigen are allowed to get into contact with bacterial lipopolysaccharide. Wherein, the bacterial lipopolysaccharide is a conventional immune-stimulating agent, and may be obtained commercially. The dosage of the bacterial lipopolysaccharide is not particularly required. Further preferably, with respect to $10^6$ of immature dendritic cells after in contact with tumor antigen, the dosage of bacterial lipopolysaccharide is 1-500 μg, more preferably 10-100 μg.

Wherein, the immature dendritic cells after in contact with tumor antigen are allowed to get into contact with the bacterial lipopolysaccharide under conventional condition for cell culture, e.g., at a temperature of 4-42° C. There is no particular requirement regarding the time of such contact, as long as the immature dendritic cells can be induced into mature dendritic cells. Typically, the time of contact may be 1-96 h.

The preparation method based on the present invention, wherein, in step (4), method to separate the membrane vesicle of said mature dendritic cells may be conventional method to separate membrane vesicle, such as differential centrifugation and/or density gradient centrifugation, e.g., the method for separating membrane vesicle recorded in Trajkovic K, et al., *Science*, 2008, 319, 1244-1247). Preferably, it comprises the following steps: (a) in homogenate buffer, said mature dendritic cells are homogenized at a homogenate clearance of 0.0005-0.0055 inch, to obtain a homogenate product; said phosphate buffer is an aqueous solution containing 12-16 mM sodium phosphate, 135-139 mM sodium chloride, 2-4 mM potassium chloride and 8-12 mM ethylenediamine tetraacetic acid, with pH of 7.5-8.5; (b) said homogenate product is centrifuged at 400-600×g for 5-15 minutes, to obtain a first supernatant; (c) said first supernatant is centrifuged at 9000-10000×g for 25-35 min, to obtain a second supernatant; (d) said second supernatant is centrifuged at 90000-110000×g for 60-80 minutes, and the resulting precipitate is membrane vesicle of said mature dendritic cells. Wherein, a homogenate clearance of 0.0005-0.0055 inch can be achieved using Dounce homogenizer.

The preparation method based on the present invention, wherein, said phosphate buffer and/or said homogenate buffer may contain protease inhibitor.

The present invention also provides an antigen composition obtained though the preparation method described above.

The present invention also provides use of above antigen composition in preparation of tumor vaccine.

The present invention also provides a tumor vaccine comprising above antigen composition and immunoadjuvant.

The tumor vaccine based on the present invention, wherein, the weight ratio of said antigen composition to immunoadjuvant may be a conventional ratio, such as 1:0.1-10.

The tumor vaccine based on the present invention, wherein, said immunoadjuvant is one or more of unmethylated CpG dinucleotides oligodeoxynucleotide (CpG ODN 1826, i.e. a nucleic acid with a sequence set forth in SEQ ID NO: 1 (5'-TCCATGACGTTCCTGACGTT-3')), malposed double-stranded ribonucleic acid (poly (I): poly (C12U) dsRNA, commercially available from Macgene, product No. tlrl-pic-5) and granulocyte colony stimulating factor (GM-CSF, commercially available from PeproTech, product No. 315-03).

The present invention will be detailed through examples as following. In the following examples, components of the phosphate buffer are 137 mM sodium chloride, 2.7 mM potassium chloride, 4.3 mM disodium hydrogen phosphate, and 1.4 mM sodium dihydrogen phosphate, with pH of 7.4-7.6.

Example 1

Antigen composition of the present invention is prepared according to the following steps in this example.

(1) The melanoma cells (cells purchased from ATCC, product No. CRL-6475) is incubated in RPMI 1640 medium (purchased from HyClone, product No. SH30809.01B, and containing 10% of fetal calf serum by volume) and 5% of $CO_2$ by volume at 37° C., until the bottom of the bottle is substantially covered with cells. The medium is removed, cells are scraped and suspended in phosphate buffer, to obtain a suspension of melanoma cells (the volume of the melanoma cell suspension is adjusted with phosphate buffer, so that the cell concentration is $5 \times 10^6$ cells/mL). The melanoma cell suspension is treated by ultrasonic waves (with respect to 1 mL of liquid to be sonicated, the ultrasonic power is 12 W; the ultrasonic frequency is 20 kHz, and time of the ultrasonic treatment is 180 s), to break the cells. And then the material which underwent ultrasonic treatment is centrifuged at 10000×g for 30 minutes. The precipitate is discarded, and the supernatant is a solution of soluble protein from melanoma cells (the volume of the melanoma cell suspension is adjusted with phosphate buffer, so that the protein concentration is 5 µg/µl).

Lung adenocarcinoma cells (cells purchased from ATCC, product No. CRL-1642) is incubated in RPMI 1640 medium (purchased from HyClone, product No. SH30809.01B, and containing 10% of fetal calf serum by volume) and 5% of $CO_2$ by volume at 37° C., until the bottom of the bottle is substantially covered with cells. The medium is removed, cells are scraped and suspended in phosphate buffer, to obtain a suspension of lung adenocarcinoma cells (the volume of the lung adenocarcinoma cell suspension is adjusted with phosphate buffer, so that the cell concentration is $5 \times 10^6$ cells/mL). The lung adenocarcinoma cell suspension is treated by ultrasonic waves (with respect to 1 mL of liquid to be sonicated, the ultrasonic power is 12 W; the ultrasonic frequency is 20 kHz, and time of the ultrasonic treatment is 180 s), to break the cells. And then the material which underwent ultrasonic treatment is centrifuged at 10000×g for 30 minutes. The precipitate is discarded, and the supernatant is a solution of soluble protein from lung adenocarcinoma cells (the volume of the lung adenocarcinoma cell suspension is adjusted with phosphate buffer, so that the protein concentration is 5 µg/µl).

Tumor antigen protein is obtained by mixing equal volume of solution of soluble protein from melanoma cells and solution of soluble protein from lung adenocarcinoma cells.

(2) According to the method recorded in Langenkamp A, et al., *Nature* 2000, 1, 311-316, a mouse is sacrificed. Bone marrow mononuclear cells are isolated from bone marrow of the mouse, and incubated in RPMI 1640 medium (purchased from HyClone, product No. SH30809.01B, and containing 10% of fetal calf serum by volume). The medium contains 500 U/mL of interleukin-4 (purchased from PeproTech, product No. AF-214-14) and 1000 U/mL granulocyte-macrophage colony stimulating factor (purchased from PeproTech, product No. AF-315-03). The incubation is carried out at 37° C. and in 5% of $CO_2$ by volume, until the cells exhibit surface marker phenotype characterized by CD11c negative, CD80 negative, CD86 negative, MHC class I H-$2K^d$ negative and MHC class II I-$A^d$ negative (around day six after initiation of incubation). And then tumor antigen protein is added, in total 10 µg tumor antigen protein to $1 \times 10^6$ immature dendritic cells. Continue incubating for 6 h. Add bacterial lipopolysaccharide (purchased from Sigma, product No. 110M4086V, with final concentration of 100 µg/mL), and continue incubating until the cells have surface marker phenotype characterized by CD11c positive, CD80 positive, CD86 positive, MHC class I H-$2K^d$ positive and MHC class II I-$A^d$ positive (taking about 24 h). Mature dendritic cells are obtained by centrifuging the culture solution at 400×g for 5 minutes and collecting the precipitate.

(3) Mature dendritic cells are washed with phosphate buffer. Cells are resuspended in homogenate buffer (an aqueous solution containing 14 mM sodium phosphate, 137 mM NaCl, 3 mM KCl, and 10 mM EDTA, with pH of 8.0) at a concentration of $5 \times 10^6$ cells/mL. Cells are homogenized using Dounce homogenizer for 30 times, to obtain homogenate product. Said product of the homogenate is centrifuged at 500×g for 10 minutes to obtain a first supernatant; said first supernatant is centrifuged at 8000×g for 30 minutes to obtain a second supernatant; said second centrifugation is centrifuged at 100000×g for 70 minutes. And the resulting precipitate is membrane vesicle of the mature dendritic cells.

The membrane vesicle of said mature dendritic cells is the antigen composition of the present invention.

According to the method described in Kovar M, et al., *Proceedings of the National Academy of Sciences of the United States of America* 2006, 103, 11671-11676, the membrane vesicle of mature dendritic cells obtained from this example is observed under TEM, and results is shown in FIG. 1, which indicating that particle size of the obtained membrane vesicle vaccine is 30-100 nm.

Preparation Example 1

The antigen composition prepared in Example 1 is mixed with immunoadjuvant (unmethylated CpG dinucleotides oligodeoxynucleotide, CpG ODN 1826, i.e. a nucleic acid with a sequence set forth in SEQ ID NO: 1 (5'-TCCATGACGT-TCCTGACGTT-3'), ordered from Invitrogen Corporation Shanghai Representative Office) at 1:1 by weight, to yield the tumor vaccine of the present invention.

Test Example 1

In this test example, tumor vaccine obtained from preparation example 1 is used as the test vaccine. Normal saline containing no tumor vaccine is used as a control vaccine. 50 μl of tumor vaccine obtained from preparation example 1 (each μl of vaccine contains 0.2 μg antigen composition, 0.2 μg immunoadjuvant, unmethylated CpG dinucleotide oligodeoxynucleotide (CpG ODN 1826)) is injected subcutaneously into foot back of mice (C57BL/J6 mice, purchased from Vital River Laboratories, Beijing, male, weighing 18-26 g), for immunization (day 0). 7 days later, the same dose of membrane vesicle vaccine is injected, to enhance immunization. 7 days after enhanced immunization (Day 14), the immunized mice are randomly divided into two groups, and inoculated subcutaneously with mouse melanoma cell and mouse lung adenocarcinoma cell, respectively. Then size of tumor is measured according to the methods recorded in Ahmed F, et al., *Molecular Pharmaceutics*, 2006, 3, 340-350. The results are shown in Table 1. The tumor inhibition rate refers to the proportion of mice without tumor among the total inoculated mice. The tumor vaccine of the present invention has been proved capable of simultaneously and effectively prevent occurrence of both mouse melanoma and mouse lung adenocarcinoma.

TABLE 1

| Group | Vaccine | Tumor inhibition rate (%) | | | | |
| --- | --- | --- | --- | --- | --- | --- |
| | | Day 10 | Day 15 | Day 20 | Day 25 | Day 30 |
| Melanoma | Control vaccine | 100 | 0 | 0 | 0 | 0 |
| | Test vaccine | 100 | 82.5 | 75 | 75 | 75 |
| Lung adeno-carcinoma | Control vaccine | 100 | 0 | 0 | 0 | 0 |
| | Test vaccine | 100 | 100 | 100 | 100 | 82.5 |

Example 2

Antigen composition of the present invention is prepared according to the following steps in this example.
(1) The melanoma cells (cells purchased from ATCC, product No. CRL-6475) is incubated in RPMI 1640 medium (purchased from HyClone, product No. SH30809.01B, and containing 10% of fetal calf serum by volume) and 5% of $CO_2$ by volume at 37° C., until the bottom of the bottle is substantially covered with cells. The medium is removed, cells are scraped and suspended in phosphate buffer, to obtain a suspension of melanoma cells (the volume of the melanoma cell suspension is adjusted with phosphate buffer, so that the cell concentration is $5 \times 10^6$ cells/mL).

Lung adenocarcinoma cells (cells purchased from ATCC, product No. CRL-1642) is incubated in RPMI 1640 medium (purchased from HyClone, product No. SH30809.01B, and containing 10% of fetal calf serum by volume) and 5% of $CO_2$ by volume at 37° C., until the bottom of the bottle is substantially covered with cells. The medium is removed, cells are scraped and suspended in phosphate buffer, to obtain a suspension of lung adenocarcinoma cells (the volume of the lung adenocarcinoma cell suspension is adjusted with phosphate buffer, so that the cell concentration is $5 \times 10^6$ cells/mL).

Mix equal volume of melanoma cell suspension with lung adenocarcinoma cell suspension. The mixed material is treated by ultrasonic waves (with respect to 1 mL of liquid to be sonicated, the ultrasonic power is 12 W; the ultrasonic frequency is 20 kHz, and time of the ultrasonic treatment is 180 s), to break the cells. And then the material which underwent ultrasonic treatment is centrifuged at 10000×g for 30 minutes. The precipitate is discarded, and the supernatant is a solution of tumor antigen protein (the volume is adjusted with phosphate buffer, so that the protein concentration is 5 μg/μl).

(2) According to the method recorded in Langenkamp A, et al., *Nature* 2000, 1, 311-316, dendritic cell line DC2.4 (cells purchased from Southern Cell Technology Limited Company, product No. CCL-01) is incubated in RPMI 1640 medium (purchased from HyClone, product No. SH30809.01B, and containing 10% of fetal calf serum by volume). The medium contains 500 U/mL of interleukin-4 (purchased from PeproTech, product No. AF-214-14) and 1000 U/mL granulocyte—macrophage colony stimulating factor (purchased from PeproTech, product No. AF-315-03). The incubation is carried out at 37° C. and in 5% of $CO_2$ by volume, until the cells exhibit surface marker phenotype characterized by CD11c negative, CD80 negative, CD86 negative, MHC class I H-2K$^d$ negative and MHC class II I-A$^d$ negative (around day six after initiation of incubation). And then tumor antigen protein is added, in total 10 μg tumor antigen protein to $1 \times 10^6$ immature dendritic cells. Continue incubating for 6 h. Add bacterial lipopolysaccharide (purchased from Sigma, product No. 110M4086V, with final concentration of 100 μg/mL), and continue incubating until the cells have surface marker phenotype characterized by CD11c positive, CD80 positive, CD86 positive, MHC class I H-2K$^d$ positive and MHC class II I-A$^d$ positive (taking about 24 h). Mature dendritic cells are obtained by centrifuging the culture solution at 400×g for 5 minutes and collecting the precipitate.

(3) Mature dendritic cells are washed with phosphate buffer. Cells are resuspended in homogenate buffer (an aqueous solution containing 14 mM sodium phosphate, 137 mM NaCl, 3 mM KCl, and 10 mM EDTA, with pH of 8.0) at a concentration of $5 \times 10^6$ cells/mL. Cells are homogenized using homogenizer for 30 times, to obtain homogenate product. Said product of the homogenate is centrifuged at 500×g for 10 minutes to obtain a first supernatant; said first supernatant is centrifuged at 8000×g for 30 minutes to obtain a second supernatant; said second centrifugation is centrifuged at 100000×g for 70 minutes. And the resulting precipitate is membrane vesicle of the mature dendritic cells.

The membrane vesicle of said mature dendritic cells is the antigen composition of the present invention.

According to the same measuring method as recited in Example 1, particle size of the obtained membrane vesicle vaccine in this example is 30-100 nm, which is determined by TEM.

Preparation Example 2

The antigen composition prepared in Example 2 is mixed with immunoadjuvant (malposed double-stranded ribonucleic acid (poly (I): poly (C12U) dsRNA, purchased from Macgene, product No. tlrl-pic-5) at 1:1 by weight, to yield the tumor vaccine of the present invention.

Test Example 2

In this test example, tumor vaccine obtained from preparation example 2 is used as the test vaccine. Normal saline containing no tumor vaccine is used as a control vaccine. 50 μl of membrane vesicle vaccine obtained from preparation example 2 (each μl of vaccine contains 0.2 μg antigen composition, 0.2 μg immunoadjuvant, unmethylated CpG dinucleotide oligodeoxynucleotide (CpG ODN 1826)) is injected subcutaneously into foot back of mice (C57BL/J6 mice, purchased from Vital River Laboratories, Beijing, male, weighing 18-26 g), for immunization (day 0). 7 days later, the same dose of membrane vesicle vaccine is injected, to enhance immunization. 7 days after enhanced immunization (Day 14), the immunized mice are randomly divided into two groups, and inoculated subcutaneously with mouse melanoma cell and mouse lung adenocarcinoma cell, respectively. Then size of tumor is measured according to the methods recorded in Ahmed F, et al., *Molecular Pharmaceutics*, 2006, 3, 340-350. The results are shown in Table 2. The tumor inhibition rate refers to the proportion of mice without tumor among the total inoculated mice. The tumor vaccine of the present invention has been proved capable of simultaneously and effectively prevent occurrence of both mouse melanoma and mouse lung adenocarcinoma.

TABLE 2

| Group | Vaccine | Tumor inhibition rate (%) | | | | |
|---|---|---|---|---|---|---|
| | | Day 10 | Day 15 | Day 20 | Day 25 | Day 30 |
| Melanoma | Control vaccine | 100 | 0 | 0 | 0 | 0 |
| | Test vaccine | 100 | 83.5 | 73 | 72 | 71 |
| Lung adeno-carcinoma | Control vaccine | 100 | 0 | 0 | 0 | 0 |
| | Test vaccine | 100 | 100 | 100 | 80.5 | 78.5 |

A preferred embodiment of the present invention is detailed above. However, the present invention is not limited to details of embodiments above. Within scope of the technical design of the present invention, multiple simple variations could be made to the technical scheme of the present invention. All these simple modifications are within the scope of the present invention.

Additionally, note that each specific technical features of the above described embodiments may be combined in any suitable manner, provided that no conflict will arise. In order to avoid unnecessary repetition, the present invention will no further explain various possible combinations.

Moreover, various embodiments of the present invention can also be combined arbitrarily as long as it does not stand against ideology of the invention, and they should also be considered as part of the disclosed content.

The invention claimed is:

1. A preparation method of an antigen composition, which comprises the following steps:
   (1) mixing soluble protein from melanoma cells with soluble protein from lung adenocarcinoma cells, to obtain tumor antigen protein; or mixing melanoma cells with lung adenocarcinoma cells and extracting soluble protein from the mixed cells, to obtain tumor antigen protein;
   (2) allowing said tumor antigen protein to get into contact with immature dendritic cells; said immature dendritic cells not only have surface marker phenotype characterized by CD11c negative, CD80 negative, CD86 negative, MHC class I H-$2K^d$ negative and MHC class II I-$A^d$ negative, but also have antigen-presenting activity;
   (3) after contacting with tumor antigen protein, inducing the immature dendritic cells into mature dendritic cells; said mature dendritic cells have surface marker phenotype characterized by CD11c positive, CD80 positive, CD86 positive, MHC class I H-$2K^d$ positive and MHC class II I-$A^d$ positive, wherein the condition under which the immature dendritic cells are induced into mature dendritic cells after contacting with tumor antigen protein includes: the immature dendritic cells after being in contact with tumor antigen protein are allowed to get into contact with bacterial lipopolysaccharide; with respect to $10^6$ of immature dendritic cells after in contact with tumor antigen protein, the dosage of bacterial lipopolysaccharide is 1-500 μg;
   (4) separating membrane vesicle of said mature dendritic cells.

2. The preparation method according to claim 1, wherein in step (1), weight ratio of said soluble protein from melanoma cells to said soluble protein from lung adenocarcinoma cells is 1:0.1-10; or ratio of the number of said melanoma cells to the number of said lung adenocarcinoma cells is 1:0.1-10.

3. The preparation method according to claim 1, wherein in step (2), with respect to $10^6$ of said immature dendritic cells, the dosage of said tumor antigen protein is 1-100 µg.

4. The preparation method according to claim 1, wherein in step (4), the method to separate the membrane vesicle of said mature dendritic cells comprises the following steps:
   (a) in homogenate buffer, said mature dendritic cells are homogenized at a homogenate clearance of 0.0005-0.0055 inch, to obtain a homogenate product; said homogenate buffer is an aqueous solution containing 12-16 mM sodium phosphate, 135-139 mM sodium chloride, 2-4 mM potassium chloride and 8-12 mM ethylenediamine tetraacetic acid, with pH of 7.5-8.5;
   (b) said homogenate product is centrifuged at 400-600×g for 5-15 minutes, to obtain a first supernatant;
   (c) said first supernatant is centrifuged at 9000-10000×g for 25-35 minutes, to obtain a second supernatant;
   (d) said second supernatant is centrifuged at 90000-110000×g for 60-80 minutes, and the resulting precipitate is membrane vesicle of said mature dendritic cells.

5. The preparation method according to claim 1, wherein said immature dendritic cell may be derived from dendritic cell line DC2.4 and/or primary bone marrow mononuclear cell.

6. The preparation method according to claim 1, wherein in step (1), weight ratio of said soluble protein from melanoma cells to said soluble protein from lung adenocarcinoma cells is 1:0.1-10; or ratio of the number of said melanoma cells to the number of said lung adenocarcinoma cells is 1:0.1-10;
   in step (2), with respect to $10^6$ of said immature dendritic cells, the dosage of said tumor antigen protein is 1-100 µg.

7. The preparation method according to claim 1, wherein in step (1), weight ratio of said soluble protein from melanoma cells to said soluble protein from lung adenocarcinoma cells is 1:0.1-10; or ratio of the number of said melanoma cells to the number of said lung adenocarcinoma cells is 1:0.1-10;
   in step (2), with respect to $10^6$ of said immature dendritic cells, the dosage of said tumor antigen protein is 1-100 µg;
   in step (3), the condition under which the immature dendritic cells are induced into mature dendritic cells after contacting with tumor antigen protein includes: the immature dendritic cells after in contact with tumor antigen protein are allowed to get into contact with bacterial lipopolysaccharide; with respect to $10^6$ of immature dendritic cells after in contact with tumor antigen protein, the dosage of bacterial lipopolysaccharide is 1-500 µg.

8. The preparation method according to claim 1, wherein in step (1), weight ratio of said soluble protein from melanoma cells to said soluble protein from lung adenocarcinoma cells is 1:0.1-10; or ratio of the number of said melanoma cells to the number of said lung adenocarcinoma cells is 1:0.1-10;
   in step (2), with respect to $10^6$ of said immature dendritic cells, the dosage of said tumor antigen protein is 1-100 µg;
   in step (3), the condition under which the immature dendritic cells are induced into mature dendritic cells after contacting with tumor antigen protein includes: the immature dendritic cells after in contact with tumor antigen protein are allowed to get into contact with bacterial lipopolysaccharide; with respect to $10^6$ of immature dendritic cells after in contact with tumor antigen protein, the dosage of bacterial lipopolysaccharide is 1-500 µg;
   in step (4), the method to separate the membrane vesicle of said mature dendritic cells comprises the following steps:
   (a) in homogenate buffer, said mature dendritic cells are homogenized at a homogenate clearance of 0.0005-0.0055 inch, to obtain a homogenate product; said homogenate buffer is an aqueous solution containing 12-16 mM sodium phosphate, 135-139 mM sodium chloride, 2-4 mM potassium chloride and 8-12 mM ethylenediamine tetraacetic acid, with pH of 7.5-8.5;
   (b) said homogenate product is centrifuged at 400-600×g for 5-15 minutes, to obtain a first supernatant;
   (c) said first supernatant is centrifuged at 9000-10000×g for 25-35 minutes, to obtain a second supernatant;
   (d) said second supernatant is centrifuged at 90000-110000×g for 60-80 minutes, and the resulting precipitate is membrane vesicle of said mature dendritic cells.

9. The preparation method according to claim 1, wherein in step (1), weight ratio of said soluble protein from melanoma cells to said soluble protein from lung adenocarcinoma cells is 1:0.1-10; or ratio of the number of said melanoma cells to the number of said lung adenocarcinoma cells is 1:0.1-10;
   in step (2), with respect to $10^6$ of said immature dendritic cells, the dosage of said tumor antigen protein is 1-100 µg;
   in step (3), the condition under which the immature dendritic cells are induced into mature dendritic cells after contacting with tumor antigen protein includes: the immature dendritic cells after in contact with tumor antigen protein are allowed to get into contact with bacterial lipopolysaccharide; with respect to $10^6$ of immature dendritic cells after in contact with tumor antigen protein, the dosage of bacterial lipopolysaccharide is 1-500 µg;
   in step (4), the method to separate the membrane vesicle of said mature dendritic cells comprises the following steps:
   (a) in homogenate buffer, said mature dendritic cells are homogenized at a homogenate clearance of 0.0005-0.0055 inch, to obtain a homogenate product; said homogenate buffer is an aqueous solution containing 12-16 mM sodium phosphate, 135-139 mM sodium chloride, 2-4 mM potassium chloride and 8-12 mM ethylenediamine tetraacetic acid, with pH of 7.5-8.5;
   (b) said homogenate product is centrifuged at 400-600×g for 5-15 minutes, to obtain a first supernatant;
   (c) said first supernatant is centrifuged at 9000-10000×g for 25-35 minutes, to obtain a second supernatant;
   (d) said second supernatant is centrifuged at 90000-110000×g for 60-80 minutes, and the resulting precipitate is membrane vesicle of said mature dendritic cells;
   said immature dendritic cell may be derived from dendritic cell line DC2.4 and/or primary bone marrow mononuclear cell.

10. The preparation method according to claim 1, wherein in step (2), with respect to $10^6$ of said immature dendritic cells, the dosage of said tumor antigen protein is 1-100 µg;
   in step (3), the condition under which the immature dendritic cells are induced into mature dendritic cells after contacting with tumor antigen protein includes: the immature dendritic cells after in contact with tumor antigen protein are allowed to get into contact with bacterial lipopolysaccharide; with respect to $10^6$ of immature dendritic cells after in contact with tumor antigen protein, the dosage of bacterial lipopolysaccharide is 1-500 μg.

11. The preparation method according to claim 1, wherein in step (1), weight ratio of said soluble protein from melanoma cells to said soluble protein from lung adenocarcinoma cells is 1:0.1-10; or ratio of the number of said melanoma cells to the number of said lung adenocarcinoma cells is 1:0.1-10;

in step (3), the condition under which the immature dendritic cells are induced into mature dendritic cells after contacting with tumor antigen protein includes: the immature dendritic cells after in contact with tumor antigen protein are allowed to get into contact with bacterial lipopolysaccharide; with respect to $10^6$ of immature dendritic cells after in contact with tumor antigen protein, the dosage of bacterial lipopolysaccharide is 1-500 μg.

\* \* \* \* \*

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: The sequence is synthesized
<220> FEATURE:
<221> NAME/KEY: misc_feature
<223> OTHER INFORMATION: CpG ODN 1826

<400> SEQUENCE: 1
tccatgacgt tcctgacgtt                                             20
```